(12) United States Patent
Park et al.

(10) Patent No.: US 11,134,876 B2
(45) Date of Patent: Oct. 5, 2021

(54) IOT BASED MONITORING METHOD AND SYSTEM FOR DETECTING SEPARATION ANXIETY OF PET USING SUPPORT VECTOR MACHINE AND COMPLEX EVENT PROCESSING

(71) Applicant: Korea University Research and Business Foundation, Sejong Campus, Sejong-si (KR)

(72) Inventors: Dai Hee Park, Sejong-si (KR); Huasang Wang, Sejong-si (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 420 days.

(21) Appl. No.: 16/184,553

(22) Filed: Nov. 8, 2018

(65) Prior Publication Data

US 2020/0138355 A1    May 7, 2020

(30) Foreign Application Priority Data

Nov. 5, 2018 (KR) .......................... 10-2018-0134540

(51) Int. Cl.
| | |
|---|---|
| *A61B 5/16* | (2006.01) |
| *A61B 5/11* | (2006.01) |
| *A61B 5/00* | (2006.01) |
| *G06N 3/02* | (2006.01) |
| *G05B 19/406* | (2006.01) |

(52) U.S. Cl.
CPC ............ *A61B 5/165* (2013.01); *A61B 5/1116* (2013.01); *A61B 5/1118* (2013.01); *A61B 5/1123* (2013.01); *A61B 5/4803* (2013.01); *G05B 19/406* (2013.01); *G06N 3/02* (2013.01); *A61B 2503/40* (2013.01); *G05B 2219/31168* (2013.01)

(58) Field of Classification Search
CPC ... A61B 5/165; A61B 2503/40; A61B 5/4803; A61B 5/1123; G06N 3/02
See application file for complete search history.

(56) References Cited

U.S. PATENT DOCUMENTS

| | | | |
|---|---|---|---|
| 2006/0047187 A1* | 3/2006 | Goyal | ................. A61B 5/0022 |
| | | | 600/300 |
| 2016/0100802 A1* | 4/2016 | Newman | ................ A61B 5/117 |
| | | | 600/301 |

FOREIGN PATENT DOCUMENTS

| | | |
|---|---|---|
| JP | 2005-502937 A | 1/2005 |
| KR | 10-2016-0097492 A | 8/2016 |
| KR | 10-2018-0067107 A | 6/2018 |

OTHER PUBLICATIONS

Martiskainen et al., Cow behaviour pattern recognition using a three-dimensional accelerometer and support vector machines, Apr. 5, 2009, Applied Animal Behaviour Science (Year: 2009).*

(Continued)

*Primary Examiner* — Eric F Winakur
*Assistant Examiner* — Jasim Ahmad Naeem
(74) *Attorney, Agent, or Firm* — Christensen O'Connor Johnson Kindness PLLC

(57) ABSTRACT

Disclosed is a method and system for monitoring a separation anxiety of a pet that may recognize an activity of the pet using a support vector machine (SVM) based on pet-related data acquired from a sensor, and may determine whether the pet is in a separation anxiety state by analyzing input data that is the recognized activity of the pet using a complex event processing (CEP).

9 Claims, 8 Drawing Sheets

(56) References Cited

OTHER PUBLICATIONS

Korean Office Action dated May 29, 2020, issued in Korean Application No. 10-2018-0134540, filed Nov. 5, 2018, 4 pages.

* cited by examiner

IOT BASED MONITORING METHOD AND SYSTEM FOR DETECTING SEPARATION ANXIETY OF PET USING SUPPORT VECTOR MACHINE AND COMPLEX EVENT PROCESSING

CROSS-REFERENCE TO RELATED APPLICATION

This application claims the priority benefit of Korean Patent Application No. 10-2018-0134540, filed on Nov. 5, 2018, in the Korean Intellectual Property Office, the disclosure of which is incorporated herein by reference.

BACKGROUND

1. Field of the Invention

Example embodiments relates to a method and system for monitoring a separation anxiety of a pet, and more particularly, to a method and system that may recognize an activity of a pet based on pet-related data acquired from a sensor, may analyze the recognized activity, and may determine whether the pet is in a separation anxiety state.

2. Description of the Related Art

Pet ownership may improve people's physical and mental health and also provide emotional benefits. The population of pet ownership is also rapidly increasing. With such an increase in the population of pet ownership, there is also an increase in a number of pets that are left alone while their owners are at work or absent for a long time.

When a pet, which is also a companion animal, is left alone for long hours in real life, the pet may experience a separation anxiety syndrome (hereinafter, separation anxiety). The separation anxiety indicates a problematic behavior of the pet caused by anxiety during the absence of an owner of the pet, and may be represented as a behavior of, for example, barking, etc. The separation anxiety may lead to damaging physical and mental health of the pet and also cause stress to the owner.

Accordingly, there is a need for a method and system that may precisely monitor a separation anxiety of a pet and may take an appropriate measure over the separation anxiety of the pet.

A health care apparatus for companion animal is disclosed in Korean Patent Laid-Open Publication No. 10-2018-0067107, published on Jun. 20, 2018, which describes a water dispenser and an apparatus for managing health of a companion animal using the water dispenser and a sensing pad.

The aforementioned information is provided only to help the understanding and may include contents not in the art and may not include contents conceivable by those skilled in the art.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

At least one example embodiment provides a method and system that may recognize an activity of a pet based on pet-related data acquired from a sensor using a support vector machine (SVM), may analyze input data that is the recognized activity of the pet using a complex event processing (CEP), and may determine a separation anxiety state of the pet.

At least one example embodiment also provides a method and system that may notify a user interface device that a pet is determined to be in a separation anxiety state, and may take an appropriate measure over separation anxiety of the pet in response to a command from the user interface device.

According to an aspect, there is provided a system for monitoring a separation anxiety of a pet, the system including an activity recognizer configured to recognize an activity of the pet using an SVM based on pet-related data acquired from at least one sensor; and a separation anxiety determiner configured to determine whether the pet is in a separation anxiety state by analyzing input data that is the activity of the pet recognized by the activity recognizer using a CEP.

A plurality of sensors may be provided as the at least one sensor, and at least one of the plurality of sensors is configured to be worn around the pet.

In response to a determination by the separation anxiety determiner, data indicating that the pet is in the separation anxiety state may be output to a user interface device.

The separation anxiety monitoring system may further include a separation anxiety handler configured to generate a measure command for taking a measure for relieving the separation anxiety of the pet in response to a command received through the user interface device and to transmit the measure command to at least one actuator.

The activity recognizer may be configured to recognize continuous primary activities of the pet based on data that is continuously acquired from the at least one sensor.

The separation anxiety determiner may be configured to determine whether the pet is in the separation anxiety state by analyzing the continuous primary activities using a hierarchical model.

The primary activities may include at least one of a posture activity of the pet including walking, standing, sitting, or lying; a head motion activity of the pet including head up, head down, or horizontal head movement; a voice activity of the pet including howling, barking, or whining; and a motion activity of the pet including digging or jumping.

The separation anxiety determiner may be configured to set each of the primary activities as an event of a first level, to determine an event of a second level of the pet including at least one of sniffing and head shake based on the event of the first level, to determine an event of a third level of the pet including at least one of an exploratory behavior, a play behavior, a destructive behavior, an escape behavior, and a voice behavior based on at least one of the event of the first level and the event of the second level, and to determine whether the pet is in the separation anxiety state based on at least one of sequence in which a behavior corresponding to the event of the third level occurs and frequency thereof.

The separation anxiety determiner may be configured to determine that the pet is in the separation anxiety state when the behavior of the pet corresponding to the event of the third level is determined to be continuously present for a desired period of time.

The separation anxiety determiner may be configured to determine that the pet is in the separation anxiety state when a specific behavior of the pet corresponding to the event of the third level is determined to be continuously present at least a desired number of times or when a pattern of specific behaviors is determined to be present.

The separation anxiety determiner may be configured to determine that the pet is in the separation anxiety state when the voice behavior is determined to be present as the event of the third level before or after the destructive behavior or the escape behavior.

The SVM may be a multi-class SVM.

According to another aspect, there is provided a computer-implemented method of monitoring a separation anxiety of a pet, the method including acquiring pet-related data from at least one sensor; recognizing an activity of the pet using an SVM based on the acquired pet-related data; and determining whether the pet is in a separation anxiety state by analyzing input data that is the recognized activity of the pet using a CEP.

The separation anxiety monitoring method may further include outputting, to a user interface device, data indicating that the pet is in the separation anxiety state; receiving a command from the user interface device; generating a measure command for taking a measure for relieving the separation anxiety of the pet in response to the received command; and transmitting the measure command to at least one actuator.

The recognizing may include recognizing continuous primary activities of the pet based on data that is continuously acquired from the at least one sensor.

The determining may include determining whether the pet is in the separation anxiety state by analyzing the continuous primary activities using a hierarchical model.

The primary activities may include at least one of a posture activity of the pet including walking, standing, sitting, or lying; a head motion activity of the pet including head up, head down, or horizontal head movement; a voice activity of the pet including howling, barking, or whining; and a motion activity of the pet including digging or jumping.

The determining may include setting each of the primary activities as an event of a first level; determining an event of a second level of the pet including at least one of sniffing and head shake based on the event of the first level; determining an event of a third level of the pet including at least one of an exploratory behavior, a play behavior, a destructive behavior, an escape behavior, and a voice behavior based on at least one of the event of the first level and the event of the second level; and determining whether the pet is in the separation anxiety state based on at least one of sequence in which a behavior corresponding to the event of the third level occurs and frequency thereof.

According to still another aspect, there is provided a system for monitoring a separation anxiety of a pet, the system including a plurality of sensors configured to collect pet-related data, at least one of the sensors being worn around the pet; an activity recognizer configured to recognize an activity of the user using an SVM based on the pet-related data acquired from the plurality of sensors; a separation anxiety determiner configured to determine whether the pet is in a separation anxiety state by analyzing input data that is the activity of the pet recognized by the activity recognizer using a CEP; a user interface device configured to receive data indicating that the pet is in the separation anxiety state, output from the separation anxiety determiner based on a determination of the separation anxiety determiner, and to output a command for an measure for the separation anxiety state; a separation anxiety handler configured to receive the command output from the user interface device, to generate a measure command for taking a measure for relieving the separation anxiety of the pet, and to transmit the measure command to at least one actuator; and the at least one actuator configured to take the measure for relieving the separation anxiety of the pet in response to the measure command.

According to example embodiments, a system for monitoring a separation anxiety of a pet may precisely recognize an activity of a pet by analyzing pet-related data that is continuously acquired from a sensor using an SVM, and may precisely verify a behavior of the pet associated with the separation anxiety by analyzing the recognized activity through a CEP using a hierarchical model.

Also, according to example embodiment, a system for monitoring a separation anxiety of a pet based on Internet of Things (IoT) may monitor a separation anxiety of a pet by analyzing data that is acquired from a plurality of sensors worn around the pet, such that a user may take an appropriate measure for relieving the determined separation anxiety at a remote location.

Further areas of applicability will become apparent from the description provided herein. The description and specific examples in this summary are intended for purposes of illustration only and are not intended to limit the scope of the present disclosure.

DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
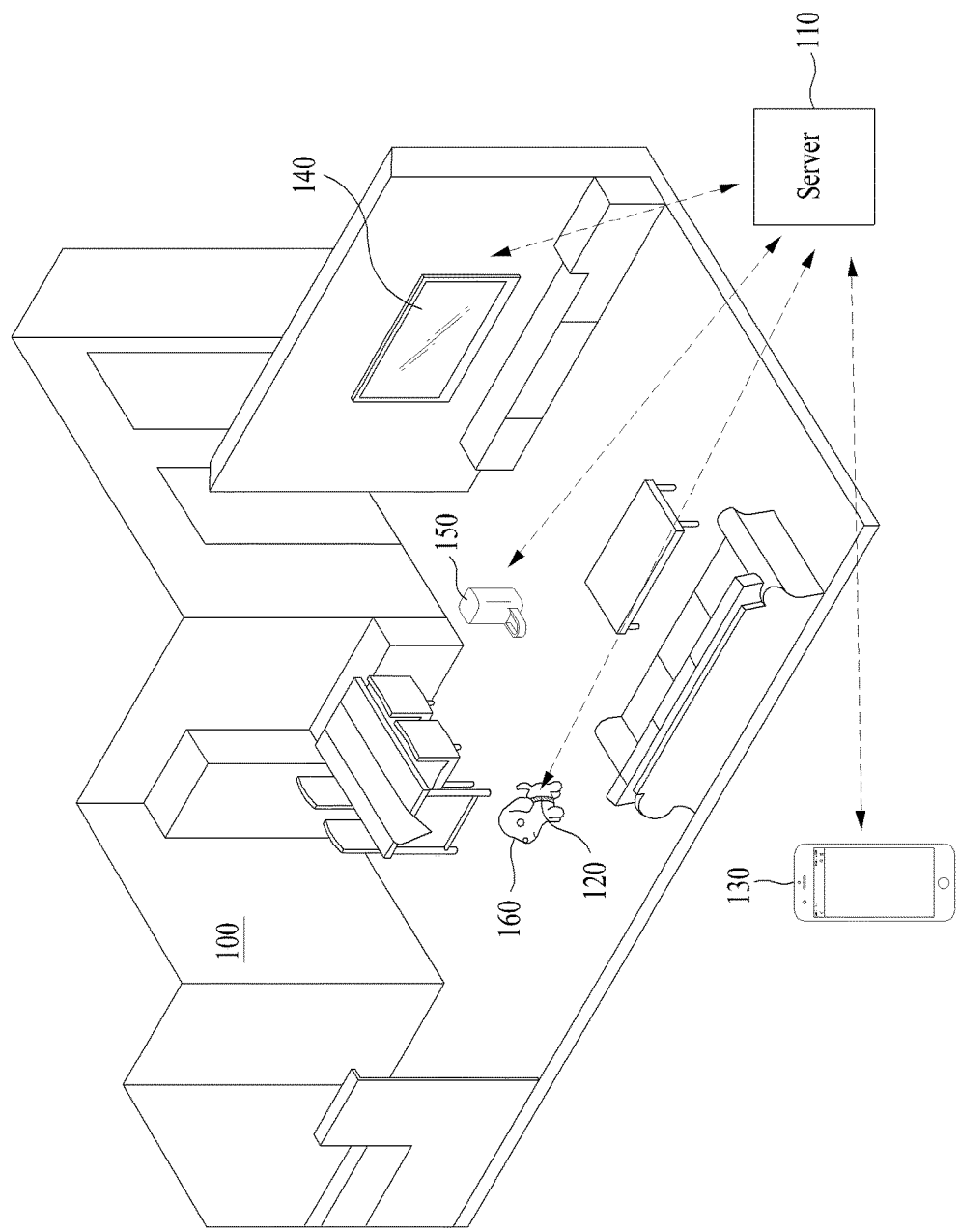
FIG. 1 illustrates an example of an environment of a system for monitoring a separation anxiety of a pet according to an example embodiment.

One or more example embodiments will be described with reference to the accompanying drawings. Advantages and features of the example embodiments, and methods for achieving the same may become explicit by referring to the accompanying drawings and the following example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated.

Terms such as first, second, A, B, (a), and (b) may be used herein to describe components. However, such terms are not used to define an essence, order, or sequence of a corresponding component, but are used merely to distinguish the corresponding component from other components. For example, a component referred to as a first component may be referred to instead as a second component, and another component referred to as a second component may be referred to instead as a first component.

The terminology used herein is for the purpose of describing particular examples only, and is not intended to limit the disclosure or claims. The singular forms "a," "an," and "the" include the plural forms as well, unless the context clearly indicates otherwise. The terms "comprises," "comprising," "includes," and "including" specify the presence of stated features, numbers, operations, elements, components, or combinations thereof, but do not preclude the presence or addition of one or more other features, numbers, operations, elements, components, or combinations thereof.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Hereinafter, the example embodiments are described with reference to the accompanying drawings in which like reference numerals refer to like elements throughout.

FIG. 1 illustrates an example of an environment of a system (hereinafter, also referred to as a separation anxiety monitoring system) for monitoring a separation anxiety of a pet according to an example embodiment.

Hereinafter, a separation anxiety monitoring system for monitoring whether a pet 160 is in a separation anxiety state and taking an appropriate measure when the pet 160 is determined to be in the separation anxiety state will be described with reference to FIG. 1.

Referring to FIG. 1, the pet 10 that is also a companion animal may be a dog or a puppy. Alternatively, the pet 160 may be a cat or another pet. A house 100 may be a space in which the pet 160 and an owner of the pet 160 live together. Herein, the owner may be absent and the pet 160 may be left alone in the house 100.

At least one sensor may be installed in the house 100 and may collect data (hereinafter, also referred to as pet-related data) related to the pet 160, for example, acceleration data by a motion of the pet 160. The at least one sensor may include a sensor 120 worn around the pet 160. That is, the sensor 120 may be a wearable device. The sensor 120 may be configured as a part of, for example, an accessory, clothes, or a leash worn around the pet 160.

A server 110 may refer to a computer apparatus that is present outside or inside the house 100, and may determine whether the pet 160 is in a separation anxiety state by acquiring data collected by the sensor 120 and by analyzing the acquired data.

When the pet 160 is determined to be in the separation anxiety state, the server 110 may transmit, to a user terminal 130 of the owner, data indicating that the pet 160 is in the separation anxiety state.

The user terminal 130 may output an alert or a notification indicating that the pet 160 is in the separation anxiety state to notify the owner of a state of the pet 160.

The owner may transmit, to the server 110 through the user terminal 130, a command for taking a measure for relieving the separation anxiety state of the pet 160. In response to the received command, the server 110 may transmit a control command to a television (TV) 140 or a food feeder 150 in the house 100. For example, in response to the control command, the TV 140 may output video or sound and the food feeder 150 may supply food to the pet 160 to relieve the separation anxiety of the pet 160.

The separation anxiety monitoring system including the server 110 of FIG. 1 may verify whether the pet 160 is in the separation anxiety state in real time and may take a measure corresponding thereto in real time.

A method of determining, by the server 110, the separation anxiety of the pet 160 and the separation anxiety monitoring system will be further described with reference to FIGS. 2 through 8.

Figure 2:
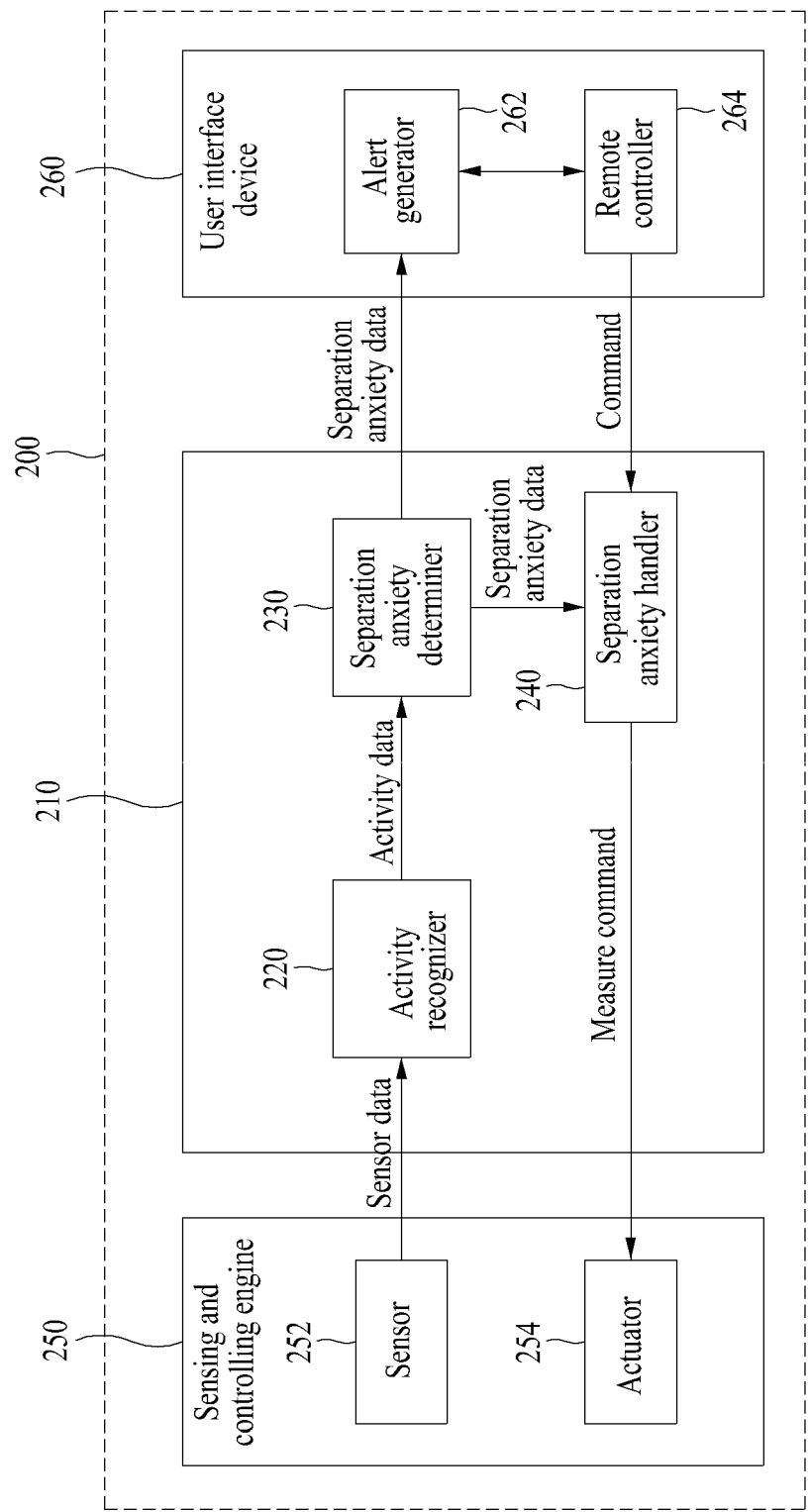
FIG. 2 is a diagram illustrating an example of a system for monitoring a separation anxiety of a pet according to an example embodiment.

FIG. 2 is a diagram illustrating an example of a system for monitoring a separation anxiety of a pet according to an example embodiment.

A separation anxiety monitoring system 200 of FIG. 2 may correspond to the separation anxiety monitoring system of FIG. 1. Also, a server 210 may correspond to the server 110, a sensor 252 included in a sensing and controlling engine 250 may correspond to the sensor 120, an actuator 254 included in the sensing and controlling engine 250 may correspond to the TV 140 and the food feeder 150, and a user interface device 260 may correspond to the user terminal 130.

Hereinafter, a method of determining a separation anxiety of the pet 160 will be described with reference to components of the separation anxiety monitoring system 200.

Referring to FIG. 2, the server 210 may refer to a computer apparatus that is present outside or inside the house 100 and configured to acquire data collected by the sensor 252, to analyze the acquired data, and to determine whether the pet 160 is in a separation anxiety state.

The server 210 may include an activity recognizer 220 configured to recognize an activity of the pet 160 using an SVM (i,e., SVM model) based on data (hereinafter, also referred to as pet-related data) related to the pet 160 acquired from the sensor 252, and a separation anxiety determiner 230 configured to determine whether the pet 160 is in the separation anxiety state by analyzing input data that is the activity of the pet 160 recognized by the activity recognizer 220 using a CEP (i.e., CEP model).

The activity recognizer 220 may classify the pet-related data collected by the sensor 252 into the activity of the pet 160 using the SVM. The SVM may be constructed in advance by performing machine learning on data, for example, sample data such as data for learning, corresponding to the pet-related data collected by the sensor 252. The activity recognizer 220 may use a plurality of SVMs to recognize or classify the activity of the pet 160. Such machine learning may be performed by the server 210 or, in addition to the server 210, by another server or other computing apparatus.

The activity recognizer 220 may recognize continuous or time serial primary activities of the pet 160 based on data that is continuously or time serially acquired from the sensor 252 using the SVM. That is, the activity recognizer 220 may classify primary activities of the pet 160 corresponding to the continuous or time series-based data acquired from the sensor 252 using the SVM.

The primary activities of the pet 160 recognized by the activity recognizer 220 may include at least one of a posture activity of the pet 160 including walking, standing, sitting, or lying; a head motion activity of the pet 160 including head up, head down, or horizontal head movement; a voice activity of the pet 160 including howling, barking, or whining; and a motion activity of the pet 160 including digging or jumping.

The SVM used by the activity recognizer 220 to classify the pet-related data collected by the sensor 252 into the activity of the pet 160 may be a multi-class SVM.

The separation anxiety determiner 230 may determine whether the pet 160 is in the separation anxiety state by analyzing the activity of the pet 160 recognized by the activity recognizer 220 using a CEP.

The separation anxiety determiner 230 may analyze continuous primary activities of the pet 160 recognized by the activity recognizer 220 using a hierarchical model. Whether the pet 160 is in the separation anxiety state may be determined by performing analysis using the hierarchical model.

For example, the separation anxiety determiner 230 may analyze continuous primary activities of the pet 160 using a hierarchical model of 4 levels. The separation anxiety determiner 230 may set each of the primary activities of the pet 160 recognized by the activity recognizer 220 as an event of a first level. The separation anxiety determiner 230 may determine an event of a second level of the pet 160 based on the event of the first level. The event of the second level may include at least one of sniffing and head shake. The separation anxiety determiner 230 may determine an event of a third level of the pet 160 based on at least one of the event of the first level and the event of the second level. The event of the third level may include at least one of an exploratory behavior, a play behavior such as an object play behavior, a destructive behavior, an escape behavior, and a voice behavior. The separation anxiety determiner 230 may determine whether the pet 160 is in the separation anxiety state based on at least one of sequence in which a behavior of the pet 160 corresponding to the event of the third level occurs and frequency thereof.

For example, the separation anxiety determiner 230 may determine that the pet 160 is in the separation anxiety state when the behavior of the pet 160 corresponding to the event of the third level is determined to be continuously present for a desired period of time. Alternatively, the separation anxiety determiner 230 may determine that the pet 160 is in the separation anxiety state when a specific behavior(s) of the pet 160 corresponding to the event of the third level is determined to be continuously present at least a desired number of times or when a pattern of specific behaviors is determined to be present. Alternatively, the separation anxiety determiner 230 may determine that the pet 160 is in the separation anxiety state when the voice behavior is determined to be present as the event of the third level before or after the destructive behavior or the escape behavior of the pet 160.

The hierarchical model of a CEP used by the separation anxiety determiner 230 to determine whether the pet 160 is in the separation anxiety state will be further described with reference to FIGS. 4 and 5.

As described above, the separation anxiety of the pet 160 may be monitored in real time by recognizing a primary activity of the pet 160 using the activity recognizer 220 based on pet-related data collected in real time by the sensor 152 and by analyzing the recognized primary activity using the separation anxiety determiner 230.

Further describing the sensor 252 configured to collect the data related to the pet 160, that is, the pet-related data, the sensor 252 may be worn around the pet 160, which is similar to the sensor 120 of FIG. 1. For example, the sensor 252 may be provided to a body and/or head of the pet 160. The sensor 252 may include a tri-axial accelerometer sensor and/or a tri-axial gyroscope sensor. The activity recognizer 220 may recognize the primary activity of the pet 160 based on the data that is acquired from the tri-axial accelerometer sensor and/or the tri-axial gyroscope sensor mounted around the body and/or head of the pet 160. Also, the sensor 252 may include a sensor configured to sense sound, for example, voice of the pet 160.

The sensor 252 may include a plurality of sensors. A portion of the plurality of sensors may be worn around the pet 160 and another portion thereof may be provided in a predetermined (or, alternatively, desired) place within the house 100.

When the separation anxiety determiner 230 determines that the pet 160 is in the separation anxiety state, data indicating that the pet 160 is in the separation anxiety state may be output to the user interface device 260.

As described above, the user interface device 260 may correspond to the user terminal 130 of FIG. 1. The user interface device 260 may refer to a terminal used by a user, such as, for example, a smartphone, a PC, a laptop computer, a tablet, an Internet of Things (IoT) device, and a wearable computer.

The user interface device 260 may include an alert generator 262 configured to generate an alert to notify the owner of the pet 160 that the pet 160 is in the separation anxiety state, in response to receiving the data indicating that the pet 160 is in the separation anxiety state. The alert generator 262 may generate the alert in such a manner that the user interface device 260 outputs sound or displays, on a display of the user interface device 260, information indicating that the pet 160 is in the separation anxiety state.

The user interface device 260 may further include a remote controller 264 configured to generate a command for a measure over the separation anxiety state of the pet 160 and to output the generated command to the server 210. The command may be generated under control of the owner over the user interface device 260 and may be a command for controlling the actuator 254.

The server 210 may further include a separation anxiety handler 240 configured to receive the command output from the user interface device 260, to generate a measure command for taking a measure for relieving the separation anxiety of the pet 160, and to transmit the measure command to the actuator 254. The actuator 254 may be controlled in response to the measure command from the separation anxiety handler 240. The measure command from the separation anxiety handler 240 may command a corrective measure or a proactive measure with respect to the separation anxiety of the pet 160. The measure command may be a control command for the actuator 254 that performs the corrective measure or the proactive measure.

The actuator 254 controlled in response to the measure command may include at least one of a speaker, a display device such as the TV 140, and the food feeder 150. For example, in response to the measure command, the TV 140 or the speaker may output audio or sound and the food feeder 150 may supply food to the pet 160 to relieve the separation anxiety of the pet 160. That is, the actuator 254 may take the measure for relieving the separation anxiety of the pet 160 in response to the measure command from the separation anxiety handler 240.

Each of the components of the server 210, for example, the activity recognizer 220, the separation anxiety determiner 230, and the separation anxiety handler 240, may be a software module and/or a hardware module as a portion of a processor of the server 210 and may represent a function or a functional block configured by the processor. Likewise, each of the alert generator 262 and the remote controller 264 of the user interface device 260 may be a software module and/or a hardware module as a portion of the user interface device 260 and may represent a function or a functional block configured by the processor.

Although not illustrated, the server 210 and the user interface device 260 may further include a communicator configured to transmit and receive information and data to and from another server/apparatus. Communication of the aforementioned sensor data, command, and data indicating the separation anxiety state may be performed among the sensing and controlling engine 250, the server 210, and the user interface device 260, that is, the components thereof. A network used for transmitting and receiving information and data is not particularly limited. For example, the network may include a mobile communication network, wired Internet, wireless Internet, a broadcasting network, a satellite network, and a near field wireless communication between devices.

The description related to technical features made above with reference to FIG. 1 may be applicable to FIG. 2, and thus a further description related thereto is omitted here.

Figure 3:
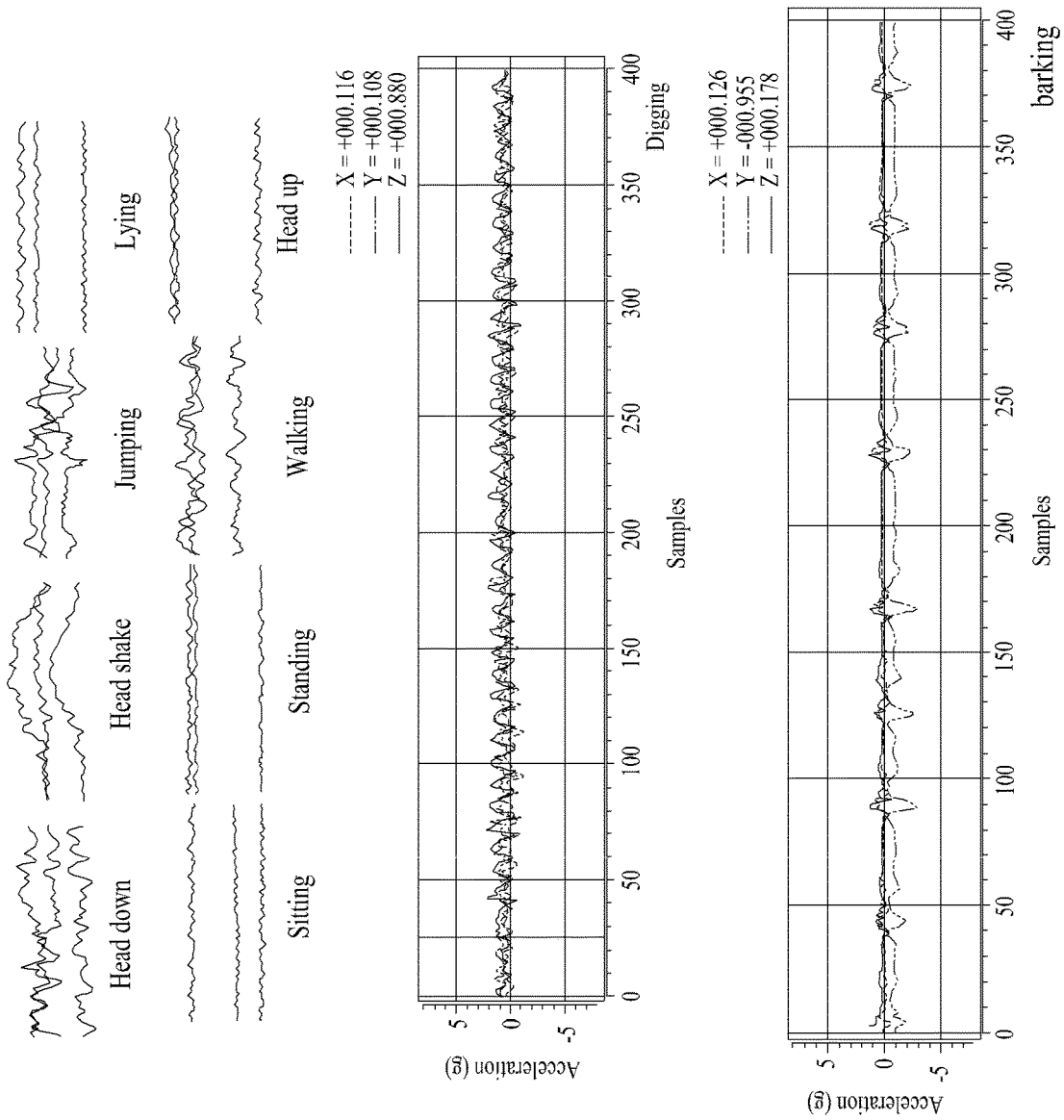
FIG. 3 illustrates an example of primary activities of a pet recognized using a support vector machine (SVM) based on an accelerometer sensor value according to an example embodiment.

FIG. 3 illustrates an example of primary activities of a pet recognized using an SVM based on an acquired accelerometer sensor value according to an example embodiment.

FIG. 3 illustrates an example of primary activities of the pet 160 recognized by the activity recognizer 220 using an SVM based on data related to the pet 160 that is acquired from the sensor 252.

Referring to FIG. 3, the activity recognizer 220 may recognize head down, horizontal head movement, jumping, lying, sitting, standing, walking, head up, digging, and barking as primary activities of the pet 160 based on data related to the pet 160 that is acquired from the sensor 252. Here, the pet-related data refers to acceleration data of x, y, and z axes.

The separation anxiety determiner 230 may use the primary activities of the pet 160 recognized by the activity recognizer 220 as input data and may determine whether the pet 160 is in a separation anxiety state by analyzing the input data using a CEP.

The description related to technical features made above with reference to FIGS. 1 and 2 may be applicable to FIG. 3, and thus a further description related thereto is omitted here.

Figure 4:
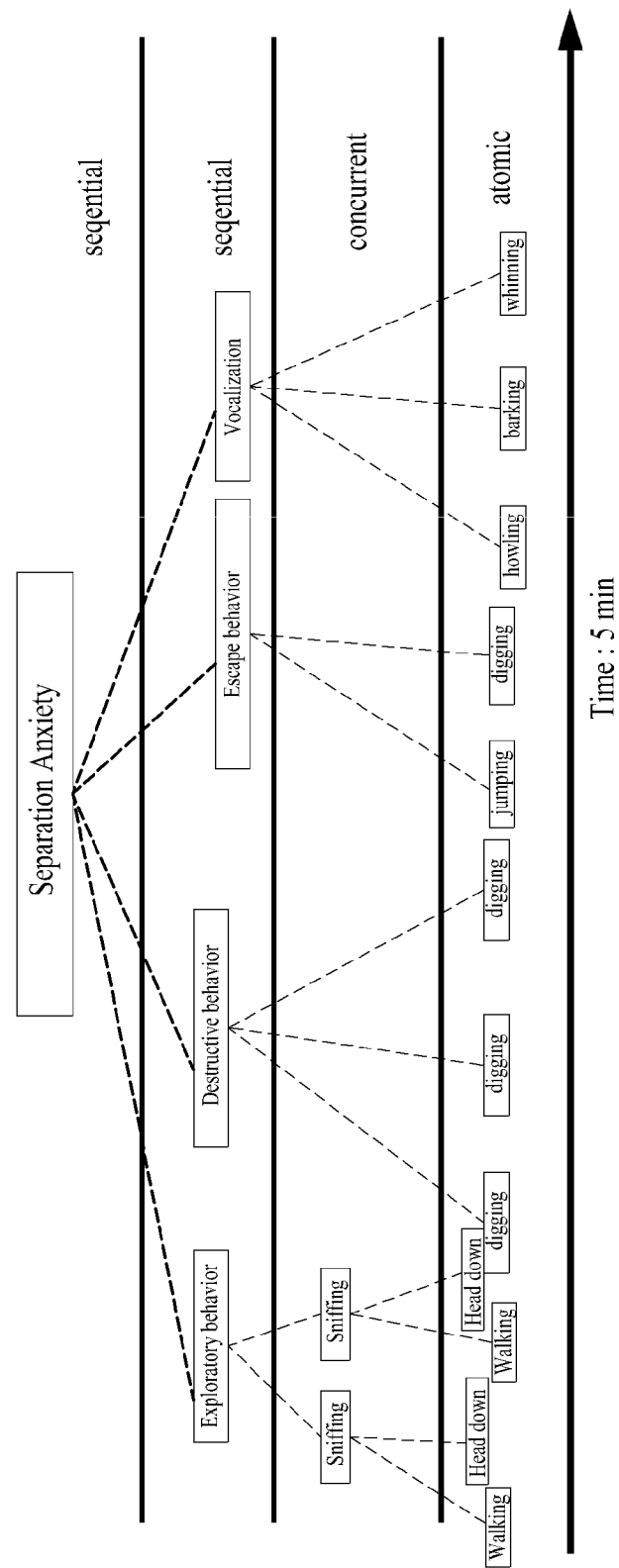
FIG. 4 illustrates an example of a hierarchical model of a complex event processing (CEP) used to analyze a recognized activity of a pet according to an example embodiment.
Figure 5:
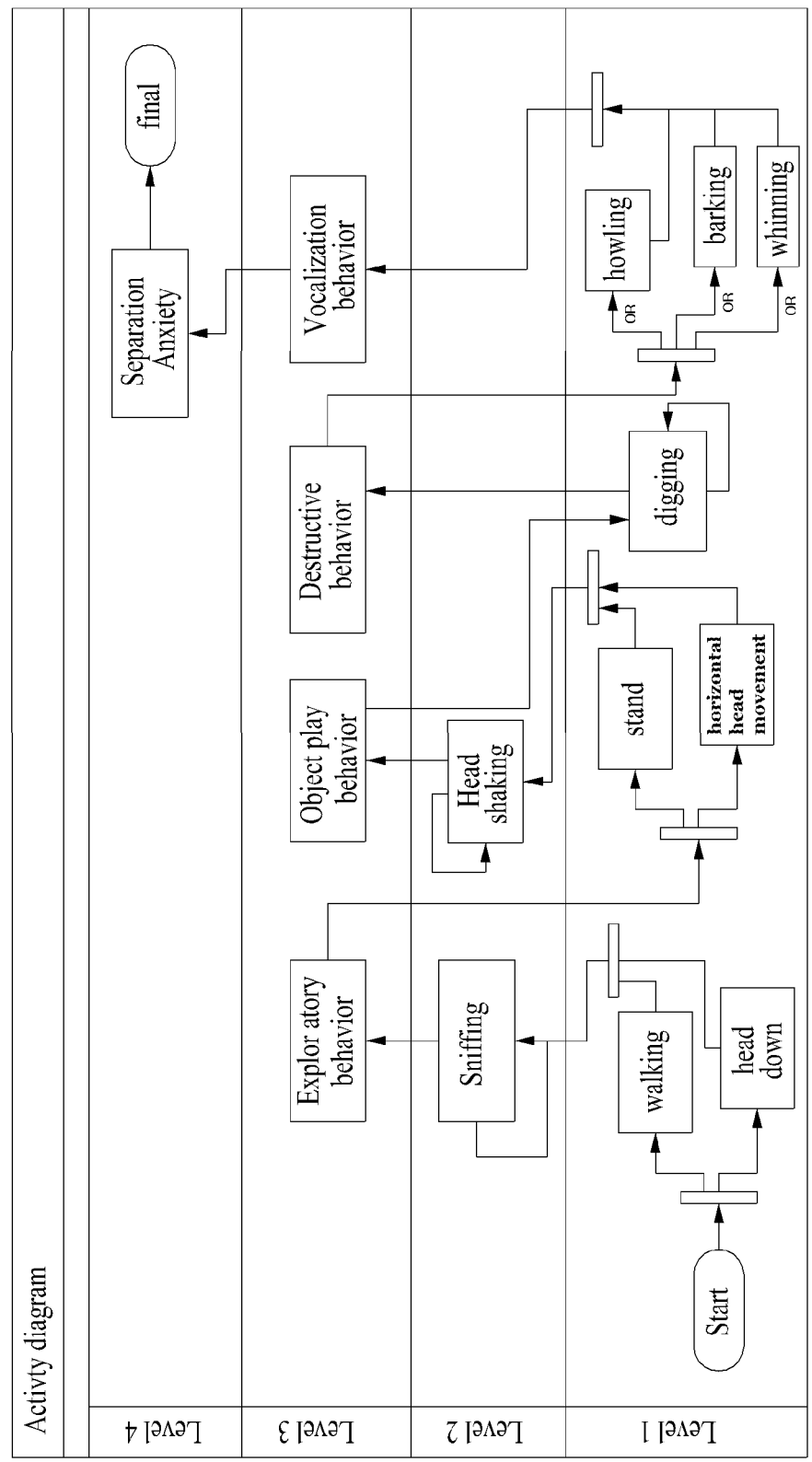
FIG. 5 illustrates an example of a 4-level hierarchical model of a CEP used to analyze a recognized activity of a pet according to an example embodiment.

FIG. 4 illustrates an example of a hierarchical model of a CEP (i.e., CEP model) used to analyze a recognized activity of a pet according to an example embodiment, and FIG. 5 illustrates an example of a 4-level hierarchical model of a CEP used to analyze a recognized activity of a pet according to an example embodiment.

The separation anxiety determiner 230 may use the hierarchical model to analyze continuous primary activities of the pet 160 recognized by the activity recognizer 220, and may determine whether the pet 160 is in a separation anxiety state based on a result of analysis performed using the hierarchical model.

Data collected by the sensor 52 may be time series-based data. In the example of FIG. 4, the primary activities of the pet 160 recognized based on data collected from the sensor 252 for 5 minutes were analyzed using the hierarchical model of the CEP.

The primary activities of the pet 160 recognized by the activity recognizer 220 may be set as an event of a first level. If head down is present after walking among the primary activities, it may be determined as sniffing that is an event of a second level. Sniffing may be determined as an exploratory behavior that is an event of a third level. Among the primary activities, if a continuous digging activity is present, digging may be determined as a destructive behavior that is the event of the third level. Among the primary activities, if a digging activity is present after jumping, jumping and digging may be determined as an escape behavior that is an event of the third level. Among the primary activities, each of howling, barking, and whining may be determined as a voice behavior that is the event of the third level. Herein, the voice behavior is also rereferred to as a vocalization.

The separation anxiety determiner 230 may determine whether the pet 160 is in the separation anxiety state based on at least one of sequence in which a behavior of the pet 160 corresponding to the event of the third level occurs and frequency thereof. For example, when a behavior of the pet 160 corresponding to the event of the third level is determined to be continuously present for a desired period of time, the separation anxiety determiner 230 may determine that the pet 160 is in the separation anxiety state. Alternatively, when specific behavior(s) of the pet 160 corresponding to the event of the third level is determined to be continuously present at least a desired number of times or when a pattern of specific patterns is determined to be present, the separation anxiety determiner 230 may determine that the pet 160 is in the separation anxiety state. Alternatively, when a voice behavior is determined to be present after a destructive behavior or an escape behavior of the pet 160 as the event of the third level, the separation anxiety determiner 230 may determine that the pet 160 is in the separation anxiety state.

FIG. 5 illustrates an example of a 4-level hierarchical model of a CEP used to analyze a recognized activity of the pet 160 further in detail.

Referring to FIG. 5, when walking and head down is recognized to be present as an event of a first level, it is determined as sniffing that is an event of a second event and sniffing is determined as an exploratory event of a third level. Subsequently, when standing and horizontal head movement is recognized to be present as the event of the first level, it is determined as head shake that is the event of the second level and head shake is determined as a play behavior that is the event of the third level. Subsequently, when digging is recognized to be present as the event of the first level, digging is determined as a destructive behavior that is the event of the third level. Subsequently, when howling, barking, or whining is recognized to be present as the event of the first level, it is determined as a voice behavior that is the event of the third level. Accordingly, the pet 160 is determined to be in the separation anxiety state, which is an event of a fourth level.

As illustrated in FIG. 5, the separation anxiety determiner 230 may determine whether the pet 160 is in the separation anxiety state by analyzing primary activities of the pet 160 recognized by the activity recognizer 220 based on time series-based data that is collected by the sensor 252, using the hierarchical model.

Figure 6:
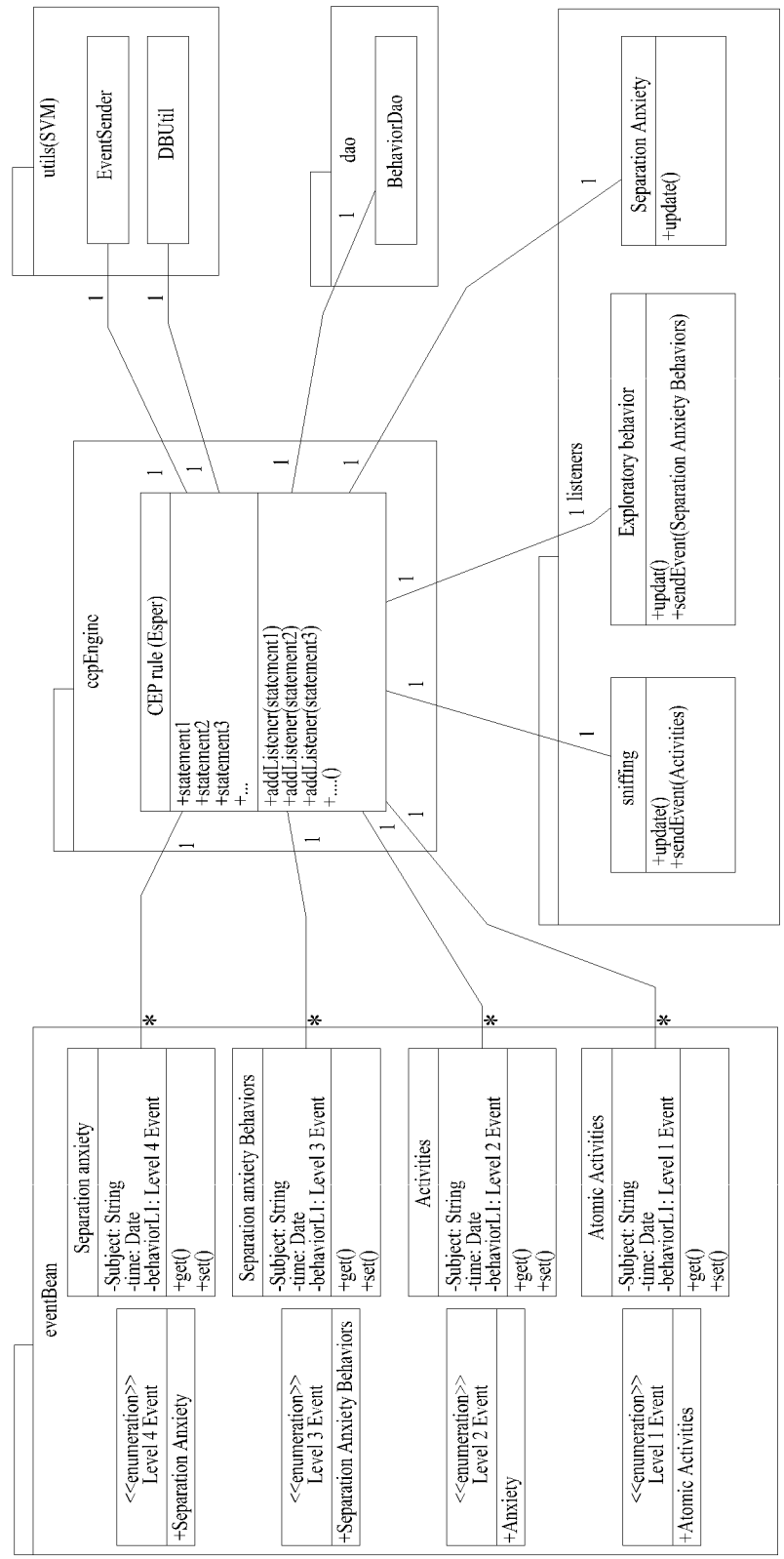
FIG. 6 illustrates an example of a CEP engine configured to analyze a recognized activity of a pet according to an example embodiment.

FIG. 6 illustrates an example of a CEP engine used to analyze a recognized activity of a pet according to an example embodiment. Referring to FIG. 6, 'eventBean' box may represent the hierarchical model described above with reference to FIGS. 4 and 5.

The description related to technical features made above with reference to FIGS. 1 to 3 may be applicable to FIG. 4, and thus a further description related thereto is omitted here.

Figure 7:
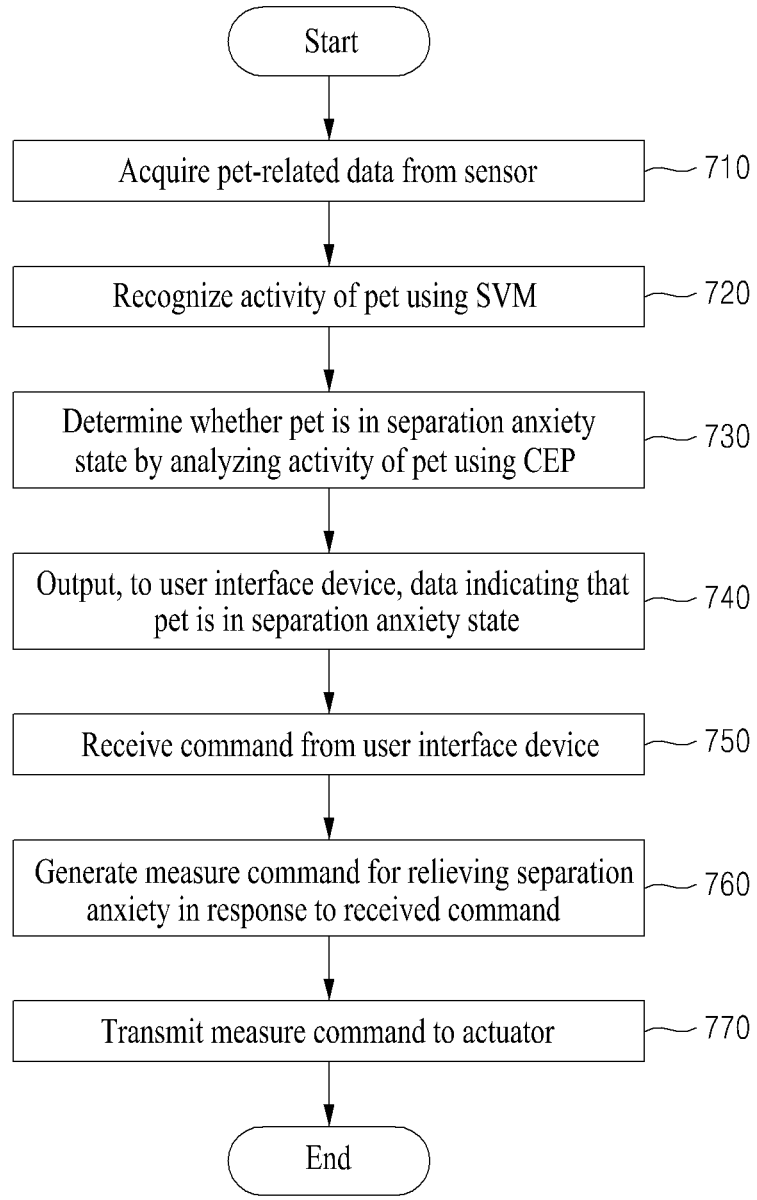
FIG. 7 is a flowchart illustrating an example of a method of monitoring a separation anxiety of a pet performed by a system for monitoring a separation anxiety of a pet according to an example embodiment.

FIG. 7 is a flowchart illustrating an example of a method of monitoring a separation anxiety of a pet performed by a system for monitoring a separation anxiety of a pet according to an example embodiment.

Hereinafter, the separation anxiety monitoring method performed by the separation anxiety monitoring system 200 will be described with reference to FIG. 7.

Referring to FIG. 7, in operation 710, the activity recognizer 220 may acquire data (also, referred to as pet-related data) related to the pet 160 from at least one sensor 252. The pet-related data may include acceleration information on a motion of the pet 160 as sensing data that is collected by the sensor 252.

In operation 720, the activity recognizer 220 may recognize an activity of the pet 160 using an SVM based on the acquired pet-related data. The activity recognizer 220 may recognize continuous or time series-based primary activities of the pet 160 based on data that is continuously or time serially acquired from the at least one sensor 252. The primary activities may include at least one of a posture activity of the pet 160 including walking, standing, sitting, or lying; a head motion activity of the pet 160 including head up, head down, or horizontal head movement; a voice activity of the pet 160 including howling, barking, or whining; and a motion activity of the pet 160 including digging or jumping.

In operation 730, the separation anxiety determiner 230 may determine whether the pet 160 is in a separation anxiety state by analyzing input data that is the recognized activity of the pet 160 using a CEP. The separation anxiety determiner 230 may determine whether the pet 160 is in the separation anxiety state by analyzing the continuous primary activities recognized by the activity recognizer 220 using a hierarchical model.

In operation 740, the separation anxiety determiner 230 may output, to the interface device 260, data indicating that the pet 160 is in the separation anxiety state. In response to receiving the data indicating that the pet 160 is in the separation anxiety state, the alert generator 262 of the user interface device 260 may generate an alert for notifying a user, for example, an owner of the pet 160, that the pet 160 is in the separation anxiety state. Also, the remote controller 264 of the user interface device 260 may generate a command for a measure for the separation anxiety state of the pet 160 and may output the generated command.

In operation 750, the separation anxiety handler 240 may receive the command output from the user interface device 260.

In operation 760, in response to the received command, the separation anxiety handler 240 may generate a measure command for taking a measure for relieving the separation anxiety of the pet 160.

In operation 770, the separation anxiety handler 240 may transmit the generated measure command to at least one actuator 254. The actuator 254 may perform the measure for relieving the separation anxiety of the pet 260 in response to the measure command from the separation anxiety handler 240.

The description related to technical features made above with reference to FIGS. 1 to 6 may be applicable to FIG. 7, and thus a further description related thereto is omitted.

Figure 8:
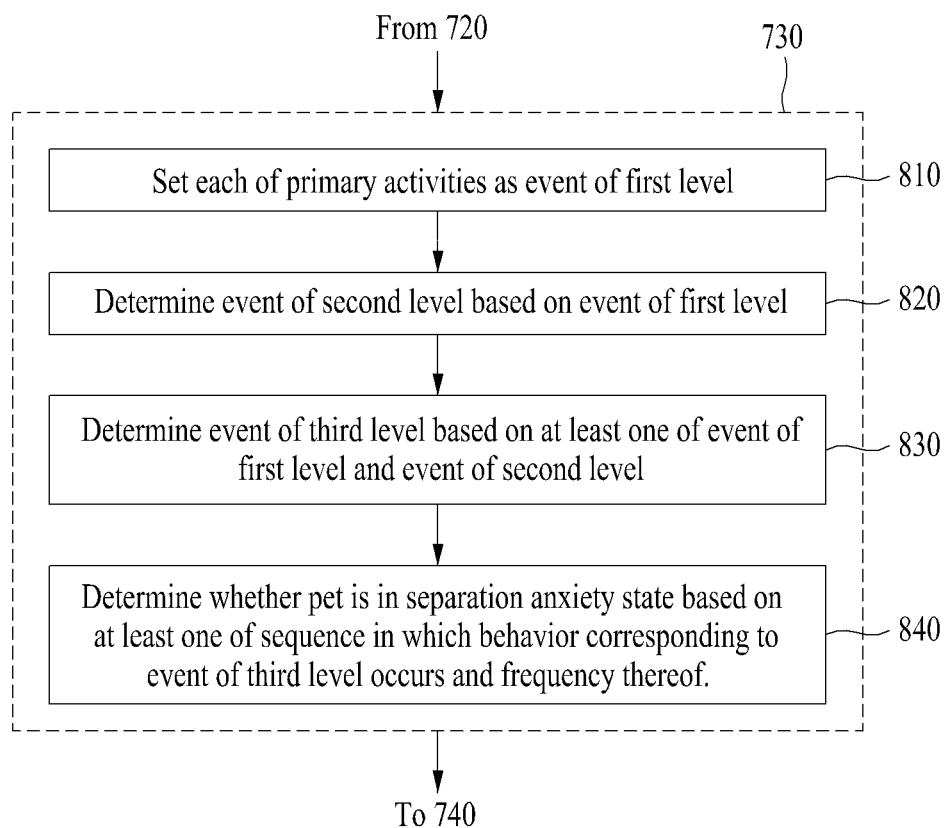
FIG. 8 is a flowchart illustrating an example of a method of determining a separation anxiety of a pet by analyzing a recognized activity of the pet using a hierarchical model of a CEP according to an example embodiment.

FIG. 8 is a flowchart illustrating an example of a method of determining a separation anxiety of a pet by analyzing a recognized activity of the pet using a hierarchical model of a CEP according to an example embodiment Operation 730 of FIG. 7 is further described with reference to FIG. 8. Operation 730 may include operations 810 through 840.

Referring to FIG. 8, in operation 810, the separation anxiety determiner 230 may set each of primary activities of the pet 160 recognized by the activity recognizer 220 as an event of a first level.

In operation 820, the separation anxiety determiner 230 may determine an event of a second level of the pet 160 that includes at least one of sniffing and head shake based on the event of the first level.

In operation 830, the separation anxiety determiner 230 may determine an event of a third level that includes at least one of an exploratory behavior, a play behavior, a destructive behavior, an escape behavior, and a voice behavior based on at least one of the event of the first level and the event of the second level.

In operation 840, the separation anxiety determiner 230 may determine whether the pet 160 is in the separation anxiety state based on at least one of sequence in which a behavior corresponding to the event of the third level occurs and frequency thereof.

As described above, the separation anxiety determiner 230 may precisely verify a behavior of the pet 160 associated with separation anxiety by analyzing the activity of the pet 160 recognized by the activity recognizer 220 through a CEP using a hierarchical model.

The description related to technical features made above with reference to FIGS. 1 to 7 may be applicable to FIG. 8, and thus a further description related thereto is omitted here.

Hereinafter, an example of a separation anxiety determining method using a CEP with respect to an activity of the pet 160 recognized by the activity recognizer 220 will be described. The separation anxiety of the pet 160 may be determined according to the following algorithm:

S. A.rule (d1, d2 is dymamic Dog Behavior(Level 3)):
Input: Dog Behavior events D
Output: S. A Events S
If d1∈D->d2∈D pattern more than twice
Return s∈ S pattern is (d1->d2) and frequency c For example, if behaviors (d1, d2) corresponding to the event of the third level represent a pattern of d1->d2 in which behaviors of the pet 160 analyzed using the CEP, for example, using the aforementioned hierarchical model, occur three times or more, the pet 160 may be determined in the separation anxiety state.

Hereinafter, an example of a raw dataset collected by the sensor 252 is described. The sensor 252 may include a tri-axial accelerometer sensor and a tri-axial gyroscope sensor. An example of a raw dataset is provided as follows. The sensor 252 may be mounted to a head or a neck portion and a body portion of the pet 160. Table 1 represents a raw dataset collected by the sensor mounted around the neck portion.

TABLE 1

| Sensor Id | Time Stamp(s) | Frame Number | AccX (g) | AccY (g) | AccZ (g) | GyroX (deg/s) | GyroY (deg/s) | GyroZ (deg/S) | MagX (uT) | MagY (uT) | MagZ (uT) |
|---|---|---|---|---|---|---|---|---|---|---|---|
| 2 | 0 | 0 | 0.6075 | −0.8946 | 0.6885 | −166.165 | −158.554 | 34.3565 | 30.722 | 13.2417 | −39.6375 |
| 2 | 0.02 | 1 | 0.3396 | −0.7587 | 0.7283 | −178.714 | −194.95 | 70.7714 | 33.879 | 11.4294 | −40.5145 |
| 2 | 0.04 | 2 | −0.0562 | −0.5169 | 0.5332 | −160.888 | −204.966 | 74.0772 | 36.3929 | 9.5294 | −41.7714 |
| 2 | 0.06 | 3 | −0.2192 | −0.5326 | 0.37 | −112.817 | −176.235 | 53.4665 | 38.6144 | 8.3894 | −41.976 |
| 2 | 0.08 | 4 | −0.2733 | −0.6988 | 0.2439 | −69.6528 | −116.396 | 37.5874 | 39.6668 | 7.4247 | −42.7945 |
| 2 | 0.1 | 5 | −0.3332 | −0.789 | 0.0423 | −44.2813 | −52.2822 | 36.0966 | 40.2514 | 6.6063 | −42.6483 |

Hereinafter, a hierarchical model including three levels is described as another example of the hierarchical model of the CEP. The 3-level hierarchical model may be defined as the following Table 2. As stated in CEP alarm of Table 2, when the pet 160 is determined to perform a behavior of the second level, the separation anxiety determiner 230 may transmit data indicating the same to the user interface device 260. The user interface device 260 may output an alert that the pet 160 is in a fear state, in a disinhibition state, or in an arousal state based on the received data using the alert generator 262 of the user interface device 260.

TABLE 2

| | Event Category | Event name | CEP alarm |
|---|---|---|---|
| level 3 | Separation Anxiety | SA | send 'dog is SA' message |
| level 2 | Fear | Escape | send 'dog is fear' message |
| | Disinhibition | Destructive Exploratory | send 'dog is disinhibition' message |
| | Arousal | Vocalization | send 'dog is arousal' message |
| level 1 | Head primary activities | head up head down barking chewing | |
| | Body primary activities | walking lying sitting standing digging jumping scratching | |

The systems and or apparatuses described herein may be implemented using hardware components, software components, and/or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable storage mediums.

The methods according to the example embodiments may be recorded in non-transitory computer-readable media including program instructions to implement various operations embodied by a computer. The media may also include, alone or in combination with the program instructions, data files, data structures, and the like. The media and program instructions may be those specially designed and constructed for the purposes, or they may be of the kind well-known and available to those having skill in the computer software arts. Examples of non-transitory computer-readable media include magnetic media such as hard disks, floppy disks, and magnetic tape; optical media such as CD ROM disks and DVD; magneto-optical media such as floptical disks; and hardware devices that are specially to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be to act as one or more software modules in order to perform the operations of the above-described embodiments, or vice versa.

The foregoing description has been provided for purposes of illustration and description. It is not intended to be exhaustive or to limit the disclosure. Individual elements or features of a particular example embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system for monitoring a separation anxiety of a pet, the system comprising:
   an activity recognizer configured to recognize an activity of the pet using a support vector machine (SVM) based on pet-related data acquired from at least one sensor wherein the activity recognizer is configured to recognize continuous primary activities of the pet based on data that is continuously acquired from the at least one sensor; and a separation anxiety determiner configured to determine whether the pet is in a separation anxiety state by analyzing input data that is the activity of the pet recognized by the activity recognizer using a complex event processing (CEP), wherein the separation anxiety determiner is configured to:

determine whether the pet is in the separation anxiety state by analyzing the continuous primary activities using a hierarchical model, wherein the primary activities comprise at least one of a posture activity of the pet comprising walking, standing, sitting, or lying; a head motion activity of the pet comprising head up, head down, or horizontal head movement; a voice activity of the pet comprising howling, barking, or whining; and a motion activity of the pet comprising digging or jumping;

set each of the primary activities as an event of a first level, to determine an event of a second level of the pet comprising at least one of sniffing and head shake based on the event of the first level, to determine an event of a third level of the pet comprising at least one of an exploratory behavior, a play behavior, a destructive behavior, an escape behavior, and a voice behavior based on at least one of the event of the first level and the event of the second level, and to determine whether the pet is in the separation anxiety state based on at least one of sequence in which a behavior corresponding to the event of the third level occurs and frequency thereof; and determine that the pet is in the separation anxiety state when the voice behavior is determined to be present as the event of the third level before or after the destructive behavior or the escape behavior.

2. The system of claim 1, wherein a plurality of sensors is provided as the at least one sensor, and at least one of the plurality of sensors is configured to be worn around the pet.

3. The system of claim 1, wherein, in response to a determination by the separation anxiety determiner that the pet is in the separation anxiety state, data indicating that the pet is in the separation anxiety state is output to a user interface device, and the system further comprises:

a separation anxiety handler configured to generate a measure command for taking a measure for relieving the separation anxiety of the pet in response to a command received through the user interface device and to transmit the measure command to at least one actuator.

4. The system of claim 1, wherein the separation anxiety determiner is configured to determine that the pet is in the separation anxiety state when the behavior of the pet corresponding to the event of the third level is determined to be continuously present for a desired period of time.

5. The system of claim 1, wherein the SVM is a multi-class SVM.

6. A computer-implemented method of monitoring a separation anxiety of a pet, the method comprising:

acquiring pet-related data from at least one sensor;

recognizing an activity of the pet using a support vector machine (SVM) based on the acquired pet-related data, wherein the recognizing comprises recognizing continuous primary activities of the pet based on data that is continuously acquired from the at least one sensor; and determining whether the pet is in a separation anxiety state by analyzing input data that is the recognized activity of the pet using a complex event processing (CEP), wherein the determining comprises:

determining whether the pet is in the separation anxiety state by analyzing the continuous primary activities using a hierarchical model, wherein the primary activities comprise at least one of a posture activity of the pet comprising walking, standing, sitting, or lying; a head motion activity of the pet comprising head up, head down, or horizontal head movement a voice activity of the pet comprising howling, barking, or whining; and a motion activity of the pet comprising digging or jumping; setting each of the primary activities as an event of a first level;

determining an event of a second level of the pet comprising at least one of sniffing and head shake based on the event of the first level;

determining an event of a third level of the pet comprising at least one of an exploratory behavior, a play behavior, a destructive behavior, an escape behavior, and a voice behavior based on at least one of the event of the first level and the event of the second level; and determining whether the pet is in the separation anxiety state based on at least one of sequence in which a behavior corresponding to the event of the third level occurs and frequency thereof.

7. The method of claim 6, further comprising:

outputting, to a user interface device, data indicating that the pet is in the separation anxiety state;

receiving a command from the user interface device;

generating a measure command for taking a measure for relieving the separation anxiety of the pet in response to the received command; and transmitting the measure command to at least one actuator.

8. A non-transitory computer-readable medium storing instructions that, when executed by a processor, cause the processor to perform the method of claim 6.

9. A system for monitoring a separation anxiety of a pet, the system comprising:

a plurality of sensors configured to collect pet-related data, at least one of the sensors being worn around the pet;

an activity recognizer configured to recognize an activity of the pet using a support vector machine (SVM) based on the pet-related data acquired from the plurality of sensors, wherein the recognizing comprises recognizing continuous primary activities of the pet based on data that is continuously acquired from the at least one sensor;

a separation anxiety determiner configured to determine whether the pet is in a separation anxiety state by analyzing input data that is the activity of the pet recognized by the activity recognizer using a complex event processing (CEP), wherein the determining comprises:

determining whether the pet is in the separation anxiety state by analyzing the continuous primary activities using a hierarchical model, wherein the primary activities comprise at least one of a posture activity of the pet comprising walking, standing, sitting, or lying; a head motion activity of the pet comprising head up, head down, or horizontal head movement a voice activity of the pet comprising howling, barking, or whining; and a motion activity of the pet comprising digging or jumping setting each of the primary activities as an event of a first level;

determining an event of a second level of the pet comprising at least one of sniffing and head shake based on the event of the first level;

determining an event of a third level of the pet comprising at least one of an exploratory behavior, a play behavior, a destructive behavior, an escape behavior, and a voice behavior based on at least one of the event of the first level and the event of the second level; and determining whether the pet is in the separation anxiety state based on at least one of sequence in which a behavior corresponding to the event of the third level occurs and frequency thereof;

a user interface device configured to receive data indicating that the pet is in the separation anxiety state, output from the separation anxiety determiner based on a determination of the separation anxiety determiner, and to output a command for a measure for the separation anxiety state;

a separation anxiety handler configured to receive the command output from the user interface device, to generate a measure command for taking a measure for relieving the separation anxiety of the pet, and to transmit the measure command to at least one actuator; and the at least one actuator configured to take the measure for relieving the separation anxiety of the pet in response to the measure command.

* * * * *

UNITED STATES PATENT AND TRADEMARK OFFICE
CERTIFICATE OF CORRECTION

PATENT NO. : 11,134,876 B2  
APPLICATION NO. : 16/184553  
DATED : October 5, 2021  
INVENTOR(S) : Park et al.

Page 1 of 1

It is certified that error appears in the above-identified patent and that said Letters Patent is hereby corrected as shown below:

In the Claims

| Column | Line | |
|--------|------|--|
| 16 | 14 | change "movement" to -- movement; --. |
| 17 | 1 | change "movement" to -- movement; --. |

Signed and Sealed this  
Fifth Day of April, 2022

Drew Hirshfeld  
*Performing the Functions and Duties of the  
Under Secretary of Commerce for Intellectual Property and  
Director of the United States Patent and Trademark Office*